US009408979B2

(12) United States Patent
Veasey et al.

(10) Patent No.: US 9,408,979 B2
(45) Date of Patent: Aug. 9, 2016

(54) PEN-TYPE INJECTOR

(71) Applicant: SANOFI-AVENTIS DEUTSCHLAND GMBH, Frankfurt am Main (DE)

(72) Inventors: Robert Frederick Veasey, Warwickshire (GB); Robert Perkins, Warwickshire (GB); David Aubrey Plumptre, Worcestershire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/946,203

(22) Filed: Nov. 19, 2015

(65) Prior Publication Data

US 2016/0074590 A1 Mar. 17, 2016

Related U.S. Application Data

(60) Continuation of application No. 14/635,573, filed on Mar. 2, 2015, now Pat. No. 9,233,211, which is a continuation of application No. 13/919,251, filed on Jun. 17, 2013, now Pat. No. 9,011,391, which is a (Continued)

(30) Foreign Application Priority Data

Mar. 3, 2003 (GB) .................................. 0304822.0

(51) Int. Cl.
*A61M 5/315* (2006.01)
*A61M 5/24* (2006.01)

(52) U.S. Cl.
CPC ....... *A61M 5/31551* (2013.01); *A61M 5/31533* (2013.01); *A61M 5/31535* (2013.01);

(Continued)

(58) Field of Classification Search
CPC ..................... A61M 5/31551; A61M 5/31533; A61M 5/31535; A61M 5/31536; A61M 5/31541; A61M 5/31546; A61M 5/31585; A61M 2005/2407; A61M 2205/581; A61M 2205/582
USPC ....... 604/208–211, 68; 128/DIG. 12, DIG. 13
See application file for complete search history.

(56) References Cited

U.S. PATENT DOCUMENTS 2,717,597 A * 9/1955 Hein, Jr. .................. A61M 5/30 604/68
2,722,931 A * 11/1955 May ........................ A61M 5/30 604/68

(Continued)

FOREIGN PATENT DOCUMENTS

DE 3609555 9/1987
EP 0673482 4/1998

(Continued)

OTHER PUBLICATIONS

Reissue U.S. Appl. No. 10/442,855, "Injection Syringe", filed May 21, 2003.

(Continued)

*Primary Examiner* — Manuel Mendez
(74) *Attorney, Agent, or Firm* — McDonnell Boehnen Hulbert & Berghoff LLP (57) ABSTRACT

The present invention relates to injectors, such as pen-type injectors, that provide for administration of medicinal products from a multidose-cartridge and permit a user to set the delivery dose. The injector may include a housing, a piston rod adapted to operate through the housing, a dose dial sleeve located between the housing and the piston rod, and a drive sleeve located between the dose dial sleeve and the piston rod. The dose dial sleeve may have a helical thread of first lead and the drive sleeve may have a helical groove of second lead. The first lead of the helical thread and the second lead of the helical groove may be the same.

10 Claims, 7 Drawing Sheets

Related U.S. Application Data division of application No. 13/040,198, filed on Mar. 3, 2011, now Pat. No. 8,512,297, which is a continuation of application No. 11/483,546, filed on Jul. 11, 2006, now Pat. No. 7,918,833, which is a continuation of application No. 10/790,225, filed on Mar. 2, 2004, now abandoned.

(52) U.S. Cl.
CPC ....... *A61M5/31536* (2013.01); *A61M 5/31541* (2013.01); *A61M 5/31546* (2013.01); *A61M 5/31585* (2013.01); *A61M 5/24* (2013.01); *A61M 5/3156* (2013.01); *A61M 5/31565* (2013.01); *A61M 5/31575* (2013.01); *A61M 5/31578* (2013.01); *A61M 2005/2407* (2013.01); *A61M 2205/581* (2013.01); *A61M 2205/582* (2013.01)

(56) References Cited

U.S. PATENT DOCUMENTS

| | | |
|---|---|---|
| 4,470,317 A | 9/1984 | Sabloewski et al. |
| 4,498,904 A | 2/1985 | Turner et al. |
| 4,568,335 A | 2/1986 | Updike et al. |
| 4,585,439 A | 4/1986 | Michel |
| 4,833,379 A | 5/1989 | Kaibel et al. |
| 4,863,072 A | 9/1989 | Perler |
| 4,865,591 A | 9/1989 | Sams |
| 4,883,472 A | 11/1989 | Michel |
| 4,919,596 A | 4/1990 | Slate et al. |
| 4,936,833 A | 6/1990 | Sams |
| 4,973,318 A | 11/1990 | Holm et al. |
| 4,994,033 A | 2/1991 | Shockey et al. |
| 5,112,317 A | 5/1992 | Michel |
| 5,207,752 A | 5/1993 | Sorenson et al. |
| 5,226,895 A | 7/1993 | Harris |
| 5,246,417 A | 9/1993 | Haak et al. |
| 5,257,987 A | 11/1993 | Athayde et al. |
| 5,271,527 A | 12/1993 | Haber et al. |
| 5,279,585 A | 1/1994 | Balkwill |
| 5,279,586 A | 1/1994 | Balkwill |
| 5,281,198 A | 1/1994 | Haber et al. |
| 5,304,152 A | 4/1994 | Sams |
| 5,308,340 A | 5/1994 | Harris |
| 5,314,412 A | 5/1994 | Rex |
| 5,318,540 A | 6/1994 | Athayde et al. |
| 5,320,609 A | 6/1994 | Haber et al. |
| 5,328,486 A | 7/1994 | Woodruff |
| 5,331,954 A | 7/1994 | Rex et al. |
| 5,370,629 A | 12/1994 | Michel et al. |
| 5,383,865 A | 1/1995 | Michel |
| 5,440,976 A | 8/1995 | Giuliano et al. |
| 5,445,606 A | 8/1995 | Haak et al. |
| 5,447,150 A | 9/1995 | Bacon |
| 5,478,316 A | 12/1995 | Bitdinger et al. |
| 5,480,387 A | 1/1996 | Gabriel et al. |
| 5,492,534 A | 2/1996 | Athayde et al. |
| 5,505,704 A | 4/1996 | Pawelka et al. |
| 5,546,932 A | 8/1996 | Galli |
| 5,549,575 A | 8/1996 | Giambattista et al. |
| 5,584,815 A | 12/1996 | Pawelka et al. |
| 5,591,136 A | 1/1997 | Gabriel |
| 5,599,314 A | 2/1997 | Neill |
| 5,611,783 A | 3/1997 | Mikkelsen |
| 5,626,566 A | 5/1997 | Petersen et al. |
| 5,645,052 A | 7/1997 | Kersey |
| 5,674,204 A | 10/1997 | Chanoch |
| 5,681,285 A | 10/1997 | Ford et al. |
| 5,688,251 A | 11/1997 | Chanoch |
| 5,709,662 A | 1/1998 | Olive et al. |
| 5,716,990 A | 2/1998 | Bagshawe et al. |
| 5,743,889 A | 4/1998 | Sams |
| 5,755,692 A | 5/1998 | Manicom |
| 5,823,998 A | 10/1998 | Yamagata |
| 5,843,036 A | 12/1998 | Olive et al. |
| 5,882,718 A | 3/1999 | Pommer et al. |
| 5,898,028 A | 4/1999 | Jensen et al. |
| 5,921,966 A | 7/1999 | Bendek et al. |
| 5,928,201 A | 7/1999 | Poulsen et al. |
| 5,947,934 A | 9/1999 | Hansen et al. |
| 5,951,530 A | 9/1999 | Steengaard et al. |
| 5,954,689 A | 9/1999 | Poulsen |
| 5,961,496 A | 10/1999 | Nielsen et al. |
| 5,980,491 A | 11/1999 | Hansen |
| 5,984,900 A | 11/1999 | Mikkelson |
| 6,003,736 A | 12/1999 | Ljunggren |
| 6,004,297 A | 12/1999 | Steenfeldt-Jensen et al. |
| 6,010,485 A | 1/2000 | Buch-Rasmussen et al. |
| 6,033,376 A | 3/2000 | Rockley |
| 6,033,377 A | 3/2000 | Rasmussen et al. |
| 6,074,372 A | 6/2000 | Hansen |
| 6,083,197 A | 7/2000 | Umbaugh |
| 6,110,149 A | 8/2000 | Klitgaard et al. |
| 6,129,080 A | 10/2000 | Pitcher et al. |
| 6,146,361 A | 11/2000 | DiBiasi et al. |
| 6,193,698 B1 | 2/2001 | Kirchhofer et al. |
| 6,221,046 B1 | 4/2001 | Burroughs et al. |
| 6,221,053 B1 | 4/2001 | Walters et al. |
| 6,231,540 B1 | 5/2001 | Smedegaard |
| 6,235,004 B1 | 5/2001 | Steenfeldt-Jensen et al. |
| 6,248,090 B1 | 6/2001 | Jensen et al. |
| 6,248,095 B1 | 6/2001 | Giambattista et al. |
| 6,258,062 B1 | 7/2001 | Thielen et al. |
| 6,269,340 B1 | 7/2001 | Ford et al. |
| 6,277,097 B1 | 8/2001 | Mikkelsen et al. |
| 6,277,098 B1 | 8/2001 | Klitmose et al. |
| 6,281,225 B1 | 8/2001 | Hearst et al. |
| 6,283,941 B1 | 9/2001 | Schoenfeld et al. |
| 6,287,283 B1 | 9/2001 | Ljunggreen et al. |
| 6,302,869 B1 | 10/2001 | Klitgaard |
| 6,312,413 B1 | 11/2001 | Jensen et al. |
| 6,340,357 B1 | 1/2002 | Poulsen et al. |
| 6,514,230 B1 | 2/2003 | Munk et al. |
| 6,547,763 B2 | 4/2003 | Steenfeldt-Jensen et al. |
| 6,547,764 B2 | 4/2003 | Larsen et al. |
| 6,562,011 B1 | 5/2003 | Buch-Rasmussen et al. |
| 6,569,126 B1 | 5/2003 | Poulsen et al. |
| 6,582,404 B1 | 6/2003 | Klitgaard et al. |
| 6,605,067 B1 | 8/2003 | Larsen |
| 6,613,019 B2 | 9/2003 | Munk |
| 6,663,602 B2 | 12/2003 | Moller |
| 6,692,472 B2 | 2/2004 | Hansen et al. |
| 6,716,198 B2 | 4/2004 | Larsen |
| 6,726,661 B2 | 4/2004 | Munk et al. |
| 6,770,288 B2 | 8/2004 | Duirs |
| 6,796,970 B1 | 9/2004 | Klitmose et al. |
| 6,893,415 B2 | 5/2005 | Madsen et al. |
| 6,899,698 B2 | 5/2005 | Sams |
| 6,899,699 B2 | 5/2005 | Enggaard |
| 6,945,961 B2 | 9/2005 | Miller et al. |
| 7,008,399 B2 | 3/2006 | Larsen et al. |
| 7,090,662 B2 | 8/2006 | Wimpenny et al. |
| 7,094,221 B2 | 8/2006 | Veasey et al. |
| 7,104,972 B2 | 9/2006 | Moller et al. |
| 7,133,329 B2 | 11/2006 | Skyggebjerg et al. |
| 7,175,055 B2 | 2/2007 | Hansen et al. |
| 7,241,278 B2 | 7/2007 | Moller |
| 7,935,088 B2 | 5/2011 | Veasey et al. |
| 8,512,297 B2 | 8/2013 | Veasey et al. |
| 2002/0052578 A1 | 5/2002 | Moller |
| 2002/0077852 A1 | 6/2002 | Ford et al. |
| 2002/0120235 A1 | 8/2002 | Enggaard |
| 2003/0039679 A1 | 2/2003 | Duirs |
| 2003/0172924 A1 | 9/2003 | Staniforth et al. |
| 2004/0059299 A1 | 3/2004 | Moller et al. |
| 2004/0186431 A1 | 9/2004 | Graf et al. |
| 2004/0210199 A1 | 10/2004 | Atterbury et al. |
| 2004/0236282 A1 | 11/2004 | Braithwaite |
| 2004/0249348 A1 | 12/2004 | Wimpenny et al. |
| 2004/0260247 A1 | 12/2004 | Veasey et al. |
| 2004/0267207 A1 | 12/2004 | Veasey et al. |
| 2004/0267208 A1 | 12/2004 | Veasey et al. |
| 2005/0004529 A1 | 1/2005 | Veasey et al. |
| 2005/0019400 A1 | 1/2005 | Deveney et al. |

(56) References Cited

U.S. PATENT DOCUMENTS

| | | |
|---|---|---|
| 2005/0033244 A1 | 2/2005 | Veasey et al. |
| 2005/0055011 A1 | 3/2005 | Enggaard |
| 2005/0113765 A1 | 5/2005 | Veasey et al. |
| 2005/0205083 A1 | 9/2005 | Staniforth et al. |
| 2005/0209570 A1 | 9/2005 | Moller |
| 2005/0268915 A1 | 12/2005 | Wassenaar et al. |

FOREIGN PATENT DOCUMENTS

| | | |
|---|---|---|
| EP | 0937471 | 8/1999 |
| EP | 0937476 | 8/1999 |
| EP | 1294418 | 7/2005 |
| FR | 2583291 | 12/1986 |
| FR | 2767479 | 2/1999 |
| JP | 05-337179 | 12/1993 |
| JP | 06-296691 | 10/1994 |
| RU | 2111019 | 5/1998 |
| WO | 90/09202 | 8/1990 |
| WO | 91/10460 | 7/1991 |
| WO | 91/14467 | 10/1991 |
| WO | 96/26754 | 9/1996 |
| WO | 98/57688 | 12/1998 |
| WO | 99/16487 | 4/1999 |
| WO | 99/38554 | 8/1999 |
| WO | 01/10484 | 2/2001 |

OTHER PUBLICATIONS

Reissue U.S. Appl. No. 10/960,900, "Injection Syringe", filed Oct. 7, 2004.
Reissue U.S. Appl. No. 11/121,331, "Injection Syringe", filed May 3, 2005.
Reissue U.S. Appl. No. 11/640,610, "Injection Syringe", filed Dec. 18, 2006.
First Office Action on merits mailed Mar. 14, 2006 in U.S. Appl. No. 10/790,866 (11 pages).

* cited by examiner

FIG. 16

PEN-TYPE INJECTOR

CROSS REFERENCE TO RELATED APPLICATIONS

The present application is a continuation of U.S. patent application Ser. No. 14/635,573, filed Mar. 2, 2015, which is a continuation of U.S. patent application Ser. No. 13/919,251, filed Jun. 17, 2013, now U.S. Pat. No. 9,011,391, which is a divisional of U.S. patent application Ser. No. 13/040,198, filed Mar. 3, 2011, now U.S. Pat. No. 8,512,297, which is a continuation of U.S. patent application Ser. No. 11/483,546, filed Jul. 11, 2006, now U.S. Pat. No. 7,918,833, which is a continuation of U.S. patent application Ser. No. 10/790,225, filed Mar. 2, 2004, which claims priority to GB 0304822.0 filed Mar. 3, 2003, the entire contents of which are incorporated herein by reference.

BACKGROUND

The present invention relates to pen-type injectors, that is, to injectors of the kind that provide for administration by injection of medicinal products from a multidose cartridge. In particular, the present invention relates to such injectors where a user may set the dose.

Such injectors have application where regular injection by persons without formal medical training occurs. This is increasingly common amongst those having diabetes where self-treatment enables such persons to conduct effective management of their diabetes.

These circumstances set a number of requirements for pen-type injectors of this kind. The injector must be robust in construction, yet easy to use both in terms of the manipulation of the parts and understanding by a user of its operation. In the case of those with diabetes, many users will be physically infirm and may also have impaired vision. Where the injector is to be disposable rather than reusable, the injector should be cheap to manufacture and easy to dispose of (preferably being suitable for recycling).

SUMMARY

It is an advantage of the present invention that an improved pen-type injector is provided.

According to a first aspect of the present invention, a pen-type injector comprises a housing;
  a piston rod adapted to operate through housing;
  a dose dial sleeve located between the housing and the piston rod, the dose dial sleeve having a helical thread of first lead;
  a drive sleeve located between the dose dial sleeve and the piston rod, the drive sleeve having a helical groove of second lead;
  characterized in that the first lead of the helical thread and the second lead of the helical groove are the same.

Preferably, the piston rod has a first threaded portion at a first end and a second threaded portion at a second end;
  an insert or radially inwardly extending flange is located in the housing and through which the first threaded portion of the piston rod may rotate;
  the dose dial sleeve being rotatable with respect to the housing and the insert;
  the drive sleeve being releasably connected to the dose dial sleeve and connected to the piston rod for rotation with respect thereto along the second threaded portion of the piston rod;
  a button is located on the dose dial sleeve and rotatable with respect to the does dial sleeve; and
  clutch means are provided which upon depression of the button permit rotation between the dose dial sleeve and the drive sleeve.

Preferably, the injector further comprises a nut which is rotatable with respect to the drive sleeve and axially displaceable but not rotatable with respect to the housing.

More preferably, the drive sleeve is provided at a first end with first and second flanges with an intermediate thread between the first and second flanges, the nut being disposed between the first and second flanges and keyed to the housing by spline means. Additionally, a first radial stop may be provided on a second face of the nut and a second radial stop may be provided on a first face of the second flange.

Preferably, the first thread of the piston rod is oppositely disposed to the second thread of the piston rod.

Preferably, a second end of the clutch is provided with a plurality of dog teeth adapted to engage with a second end of the dose dial sleeve.

Preferably, the pen-type injector further includes clicker means disposed between the clutch means and spline means provided on the housing.

More preferably, the clicker means comprises a sleeve provided at a first end with a helically extending arm, a free end of the arm having a toothed member, and at a second end with a plurality of circumferentially directed saw teeth adapted to engage a corresponding plurality of circumferentially saw teeth provided on the clutch means.

Alternatively, the clicker means comprises a sleeve provided at a first end with at least one helically extending arm and at least one spring member, a free end of the arm having a toothed member, and at a second end with a plurality of circumferentially directed saw teeth adapted to engage a corresponding plurality of circumferentially directed saw teeth provided on the clutch means.

Preferably, the main housing is provided with a plurality of maximum dose stops adapted to be abutted by a radial stop provided on the dose dial sleeve. More preferably, at least one of the maximum dose stops comprises a radial stop located between a helical rib and spline means provided at a second end of the housing. Alternatively, at least one of the maximum dose stops comprises a part of a raised window portion provided at a second end of the housing.

Preferably, the dose dial sleeve is provided with a plurality of radially extending members adapted to abut a corresponding plurality of radial stops provided at a second end of the housing.

BRIEF DESCRIPTION OF THE FIGURES

The invention will now be described with reference to the accompanying drawings in which.

DETAILED DESCRIPTION

Referring first to FIGS. 1 to 5, there may be seen a pen-type injector in accordance with the present invention in a number of positions.

The pen-type injector comprises a housing having a first cartridge retaining part 2, and second main housing part 4. A first end of the cartridge retaining means 2 and a second end of the main housing 4 are secured together by retaining features 6. In the illustrated embodiment, the cartridge retaining means 2 is secured within the second end of the main housing 4.

A cartridge 8 from which a number of doses of medicinal product may be dispensed is provided in the cartridge retaining part 2. A piston 10 is retained in a first end of the cartridge 8.

A removable cap 12 is releasably retained over a second end of the cartridge retaining part 2. In use the removable cap 12 can be replaced by a user with a suitable needle unit (not shown). A replaceable cap 14 is used to cover the cartridge retaining part 2 extending from the main housing 4. Preferably, the outer dimensions of the replaceable cap 14 are similar or identical to the outer dimensions of the main housing 4 to provide the impression of a unitary whole when the replaceable cap 14 is in position covering the cartridge retaining part 2.

In the illustrated embodiment, an insert 16 is provided at a first end of the main housing 4. The insert 16 is secured against rotational or longitudinal motion. The insert 16 is provided with a threaded circular opening 18 extending therethrough. Alternatively, the insert may be formed integrally with the main housing 4 the form of a radially inwardly directed flange having an internal thread.

A first thread 19 extends from a first end of a piston rod 20. The piston rod 20 is of generally circular section. The first end of the piston rod 20 extends through the threaded opening 18 in the insert 16. A pressure foot 22 is located at the first end of the piston rod 20. The pressure foot 22 is disposed to abut a second end of the cartridge piston 10. A second thread 24 extends from a second end of the piston rod 20. In the illustrated embodiment the second thread 24 comprises a series of part threads rather than a complete thread. The illustrated embodiment is easier to manufacture and helps reduce the overall force required for a user to cause medicinal product to be dispensed.

The first thread 19 and the second thread 24 are oppositely disposed. The second end of the piston rod 20 is provided with a receiving recess 26.

A drive sleeve 30 extends about the piston rod 20. The drive sleeve 30 is generally cylindrical. The drive sleeve 30 is provided at a first end with a first radially extending flange 32. A second radially extending flange 34 is provided spaced a distance along the drive sleeve 30 from the first flange 32. An intermediate thread 36 is provided on an outer part of the drive sleeve 30 extending between the first flange 32 and the second flange 34. A helical groove 38 extends along the internal surface of the drive sleeve 30. The second thread 24 of the piston rod 20 is adapted to work within the helical groove 38.

A first end of the first flange 32 is adapted to conform to a second side of the insert 16.

A nut 40 is located between the drive sleeve 30 and the main housing 2, disposed between the first flange 32 and the second flange 34. In the illustrated embodiment the nut 40 is a half-nut. This assists in the assembly of the injector. The nut 40 has an internal thread matching the intermediate thread 36. The outer surface of the nut 40 and an internal surface of the main housing 4 are keyed together by splines 42 (see FIGS. 10, 11, 15 and 16) to prevent relative rotation between the nut 40 and the main housing 4, while allowing relative longitudinal movement therebetween.

A shoulder 37 is formed between a second end of the drive sleeve 30 and an extension 38 provided at the second end of the drive sleeve 30. The extension 38 has reduced inner and outer diameters in comparison to the remainder of the drive sleeve 30. A second end of the extension 38 is provided with a radially outwardly directed flange 39.

A clicker 50 and a clutch 60 are disposed about the drive sleeve 30, between the drive sleeve 30 and a dose dial sleeve 70 (to be described below).

Figures 1, 2:
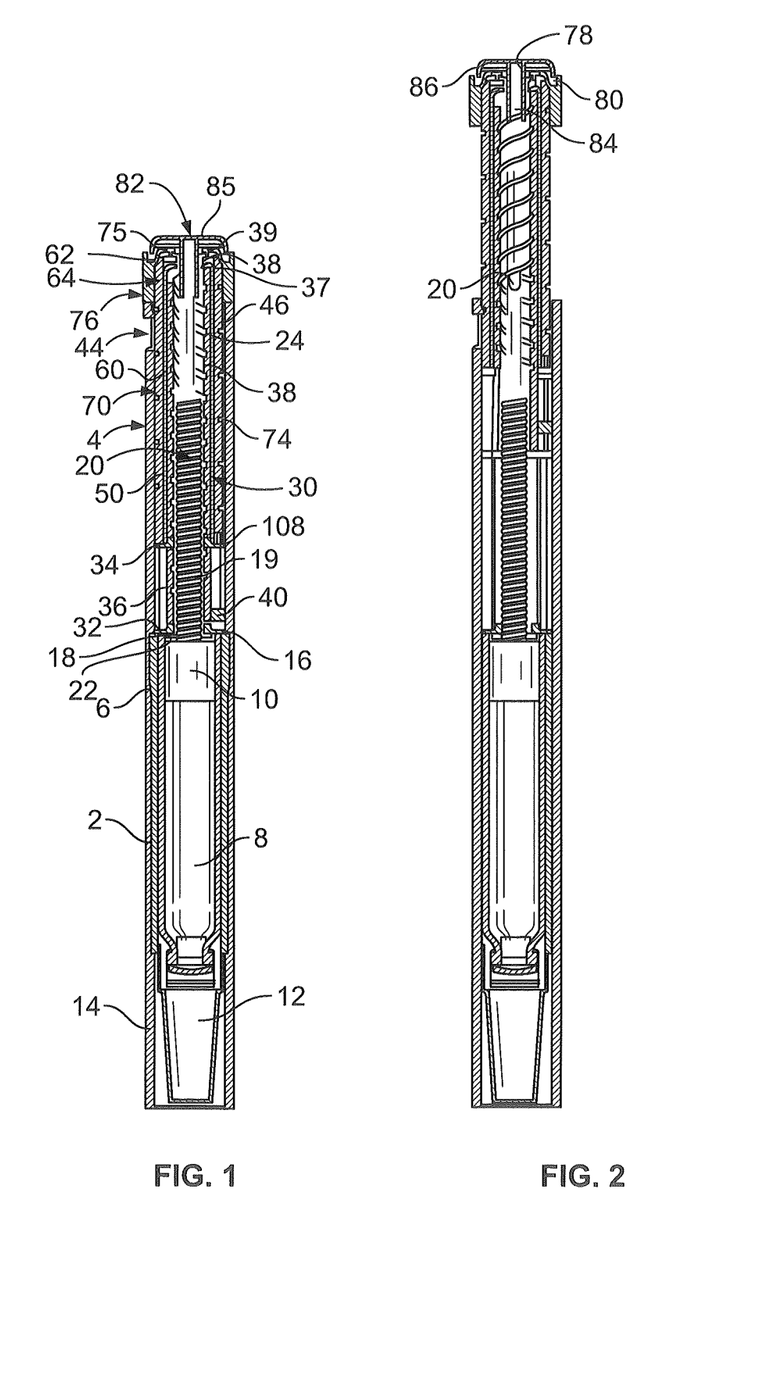
FIG. 1 shows a sectional view of a pen-type injector in accordance with the present invention in a first, cartridge full, position.
FIG. 2 shows a sectional view of the pen-type injector of FIG. 1 in a second, maximum first dose dialed, position.
Figure 3:
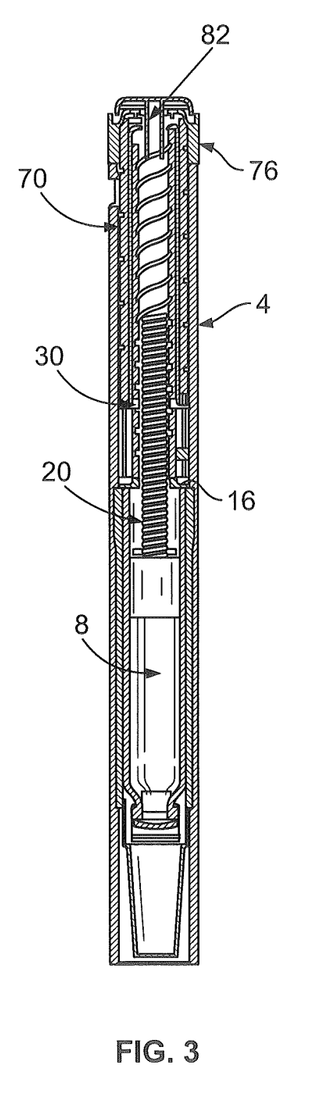
FIG. 3 shows a sectional view of the pen-type injector of FIG. 1 in a third, first maximum first dose dispensed, position.
Figure 4:
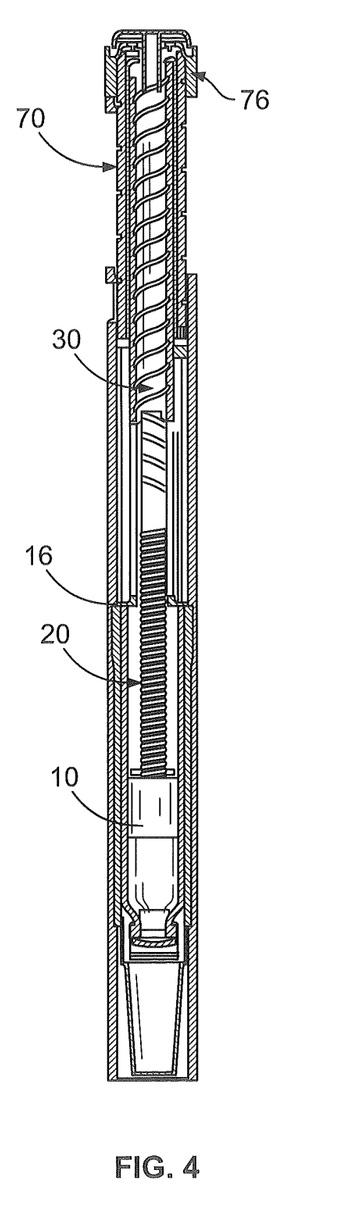
FIG. 4 shows a sectional view of the pen-type injector of FIG. 1 in a fourth, final dose dialed, position.
Figure 5:
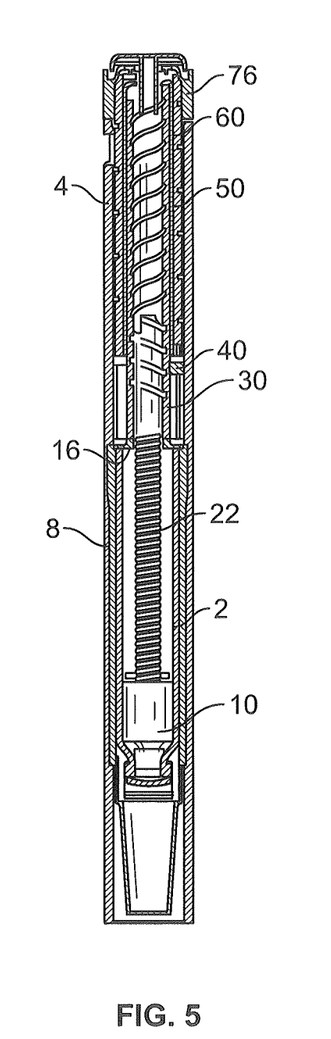
FIG. 5 shows a sectional view of the pen-type injector of FIG. 1 in a fifth, final dose dispensed, position.
Figure 6:
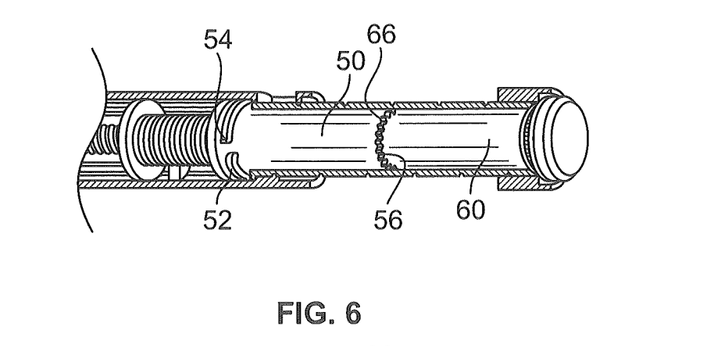
FIG. 6 shows a cut-away view of a first detail of the pen-type injector of FIG. 1.

The clicker 50 is located adjacent the second flange 34 of the drive sleeve 30. The clicker 50 is generally cylindrical and is provided at a first end with a flexible helically extending arm 52 (shown most clearly in FIG. 6). A free end of the arm 52 is provided with a radially directed toothed member 54. A second end of the clicker 50 is provided with a series of circumferentially directed saw teeth 56 (of FIG. 7). Each saw tooth comprises a longitudinally directed surface and an inclined surface.

In an alternative embodiment (not shown) the clicker means further includes at least one spring member. The at least one spring member assists in the resetting of the clutch means 60 following dispense.

The clutch means 60 is located adjacent the second end of the drive sleeve 30. The clutch means 60 is generally cylindrical and is provided at a first end with a series of circumferentially directed saw teeth 66 (see FIG. 7). Each saw tooth comprises a longitudinally directed surface and an inclined surface. Towards the second end 64 of the clutch means 60 there is located a radially inwardly directed flange 62. The flange 62 of the clutch means 60 is disposed between the shoulder 37 of the drive sleeve 30 and the radially outwardly directed flange 39 of the extension 38. The second end of the clutch means 60 is provided with a plurality of dog teeth 65 (FIG. 8). The clutch 60 is keyed to the drive sleeve 30 by way of splines (not shown) to prevent relative rotation between the clutch 60 and the drive sleeve 30.

In the illustrated embodiment, the clicker 50 and the clutch 60 each extend approximately half the length of the drive sleeve 30. However, it will be understood that other arrangements regarding the relative lengths of these parts are possible.

Figure 7:
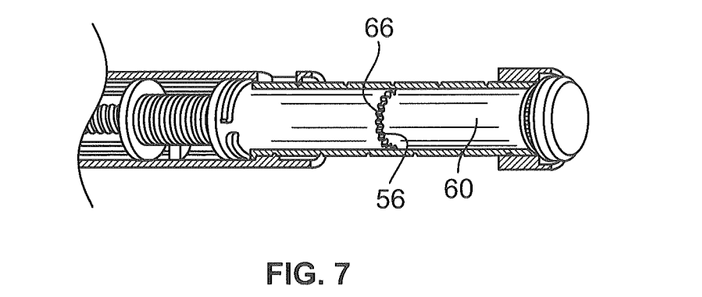
FIG. 7 shows a partially cut-away view of a second detail of the pen-type injector of FIG. 1.
Figure 8:
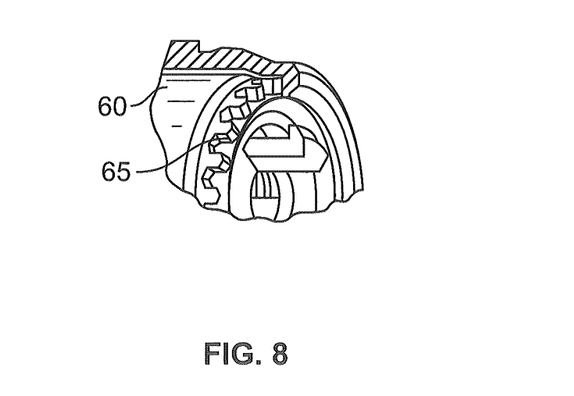
FIG. 8 shows a partially cut-away view of a third detail of the pen-type injector of FIG. 1.

The clicker 50 and the clutch means 60 are normally engaged, that is as shown in FIG. 7.

A dose dial sleeve 70 is provided outside of the clicker 50 and clutch means 60 and radially inward of the main housing 4. A helical groove 74 is provided about an outer surface of the dose dial sleeve 70.

Figure 15:
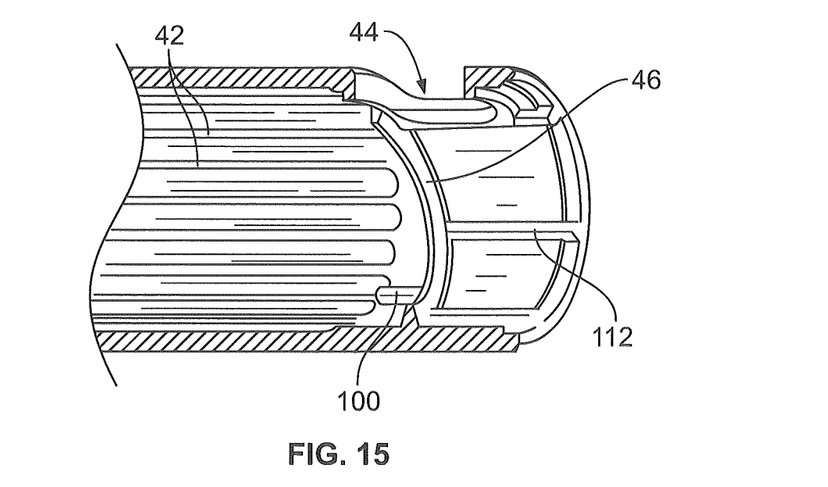
FIG. 15 shows a cut-away view of a first part of a main housing of the pen-type injector of FIG. 1.
Figure 16:
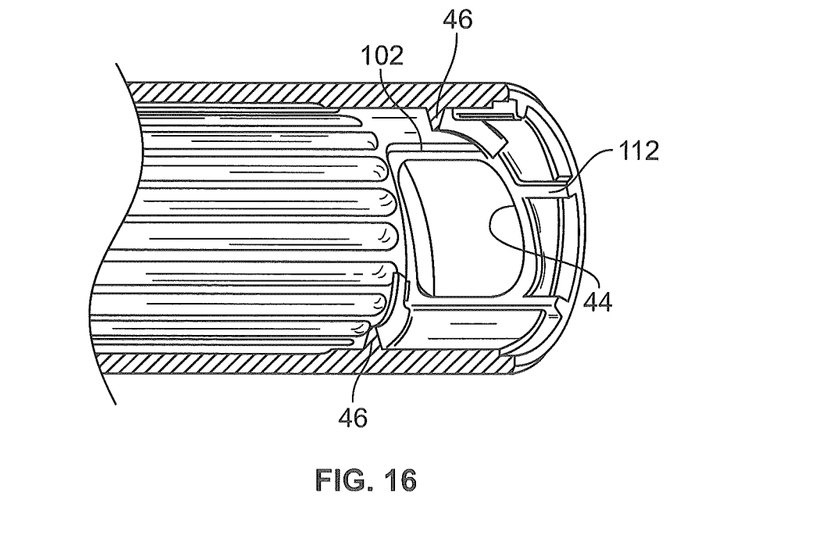
FIG. 16 shows a cut-away view of a second part of the main housing of the pen-type injector of FIG. 1.

The main housing 4 is provided with a window 44 through which a part of the outer surface of the dose dial sleeve may be seen. The main housing 4 is further provided with a helical rib 46, adapted to be seated in the helical groove 74 on the outer surface of the dose dial sleeve 70. The helical rib 46 extends for a single sweep of the inner surface of the main housing 4. A first stop 100 is provided between the splines 42 and the helical rib 46 (FIG. 15). A second stop 102, disposed at an angle of 180° to the first stop 100 is formed by a frame surrounding the window 44 in the main housing 4 (FIG. 16).

Conveniently, a visual indication of the dose that may be dialed, for example reference numerals (not shown). is provided on the outer surface of the dose dial sleeve 70. The Window 44 conveniently only allows to be viewed a visual indication of the dose currently dialed.

A second end of the dose dial sleeve 70 is provided with an inwardly directed flange in the form of number of radially extending members 75. A dose dial grip 76 is disposed about an outer surface of the second end of the dose dial sleeve 70. An outer diameter of the dose dial grip 76 preferably corresponds to the outer diameter of the main housing 4. The dose dial grip 76 is secured to the dose dial sleeve 70 to prevent relative movement therebetween. The dose dial grip 76 is provided with a central opening 78. An annular recess 80 located in the second end of the dose dial grip 76 extends around the opening 78.

A button 82 of generally 'T' section is provided at a second end of the pen-type injector. A stem 84 of the button 82 may extend through the opening 78 in the dose dial grip 76, through the inner diameter of the extension 38 of the drive sleeve 30 and into the receiving recess 26 of the piston rod 20. The stem 84 is retained for limited axial movement in the drive sleeve 30 and against rotation with respect thereto. A head 85 of the button 82 is generally circular. A skirt 86 depends from a periphery of the head 85. The skirt 86 is adapted to be seated in the annular recess 80 of the dose dial grip 76.

Figure 9:
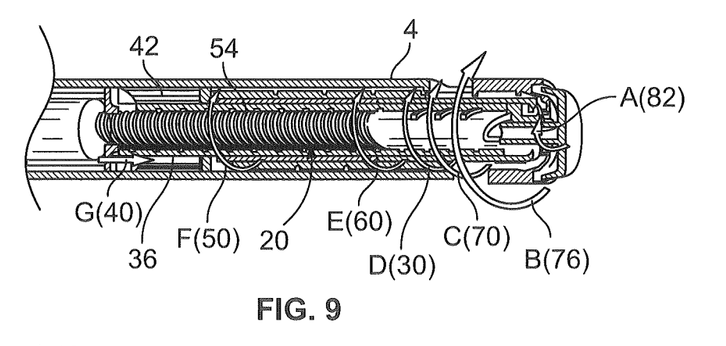
FIG. 9 shows the relative movement of parts of the pen-type injector shown in FIG. 1 during dialing up of a dose.
Figure 10:
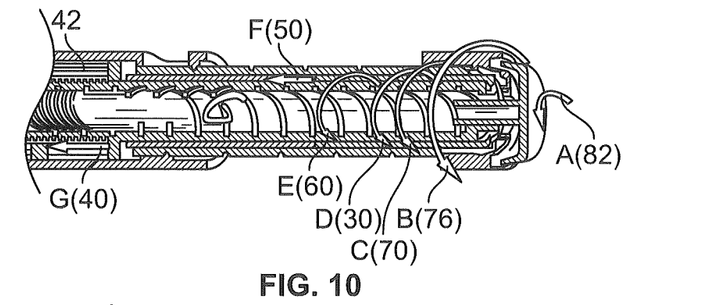
FIG. 10 shows the relative movement of parts of the pen-type injector shown in FIG. 1 during dialing down of a dose.
Figure 11:
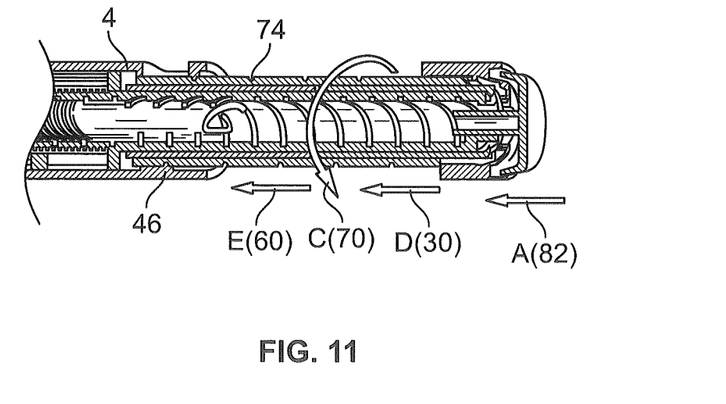
FIG. 11 shows the relative movement of parts of the pen-type injector shown in FIG. 1 during dispensing of a dose.
Figure 12:
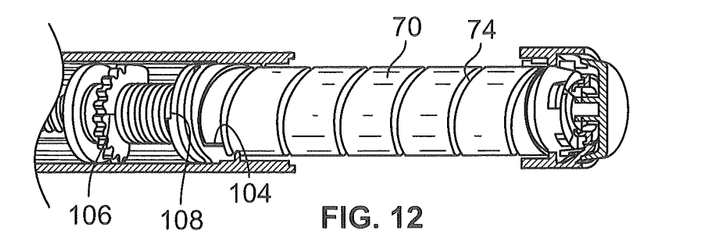
FIG. 12 shows a partially cut-away view of the pen-type injector of FIG. 1 in the second, maximum first dose dialed, position.

Operation of the pen-type injector in accordance with the present invention will now be described. In FIGS. 9, 10 and 11 arrows A, B. C, D, E, F and G represent the respective movements of the button 82, the dose dial grip 76, the dose dial sleeve 70, the drive sleeve 30, the clutch means 60, the clicker 50 and the nut 40.

To dial a dose (FIG. 9) a user rotates the dose dial grip 76 (arrow A). With the clicker 50 and clutch means 60 engaged, the drive sleeve 30, the clicker 50, the clutch means 60 and the dose dial sleeve 70 rotate with the dose dial grip 76.

Audible and tactile feedback of the dose being dialed is provided by the clicker 50 and the clutch means 60. Torque is transmitted through the saw teeth 56, 66 between the clicker 50 and the clutch means 60. The flexible arm 52 deforms and drags the toothed member 54 over the splines 42 to produce a click. Preferably, the splines 42 are dispose such that each click corresponds to a unit dose.

The helical groove 74 on the dose dial sleeve 70 and the helical groove 38 in the drive sleeve 30 have the same lead. This allows the dose dial sleeve 70 (arrow C) to extend from the main housing 4 and the drive sleeve 30 (arrow D) to climb the piston rod 20 at the same rate. At the limit of travel, a radial stop 104 on the dose dial sleeve 70 engages either the first stop 100 or the second stop 102 provided on the main housing 4 to prevent further movement. Rotation of the piston rod 20 is prevented due to the opposing directions of the overhauled and driven threads on the piston rod 20.

Figure 13:
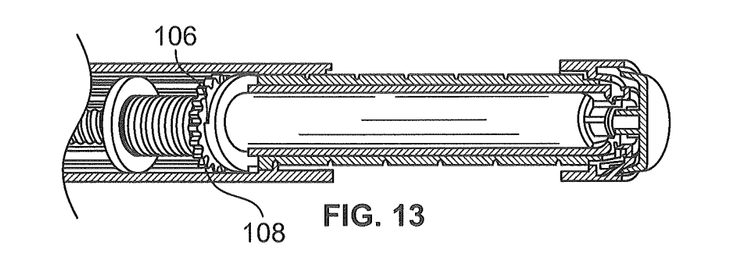
FIG. 13 shows a partially cut-away view of the pen-type injector of FIG. 1 in the fourth, final dose dialed, position.

The nut 40, keyed to the main housing 4, is advanced along the intermediate thread 36 by the rotation of the drive sleeve 30 (arrow D). When the final dose dispensed position (FIGS. 4, 5 and 13) is reached, a radial stop 106 formed on a second surface of the nut 40 abuts a radial stop 108 on a first surface of the second flange 34 of the drive sleeve 30 preventing both the nut 40 and the drive sleeve 30 from rotating further.

In an alternative embodiment (not shown) a first surface of the nut 40 is provided with a radial stop for abutment with a radial stop provided on a second surface of the first flange 32. This aids location of the nut 40 at the cartridge full position during assembly of the pen-type injector.

Should a user inadvertently dial beyond the desired dosage, the pen-type injector allows the dosage to be dialed down without dispense of medicinal product from the cartridge (FIG. 10). The dose dial grip 76 is counter rotated. This causes the system to act in reverse. The flexible arm 52 now acts as a ratchet preventing the clicker from rotating. The torque transmitted through the clutch means 60 causes the saw teeth 56,66 to ride over one another to create the clicks corresponding to dialed dose reduction. Preferably the saw teeth 56,66 are so disposed that the circumferential extent of each saw tooth corresponds to a unit dose.

When the desired dose has been dialed, the user may then dispense this dose by depressing the button 82 (FIG. 11). This displaces the clutch means 60 axially with respect to the dose dial sleeve 70 causing the dog teeth 65 to disengage. However the clutch means 60 remains keyed in rotation to the drive sleeve 30. The dose dial sleeve 70 and associated dose dial grip 76 are now free to rotate (guided by the helical rib 46 located in helical groove 74).

The axial movement deforms the flexible arm 52 of the clicker 50 to ensure the saw teeth 56,66 cannot be overhauled during dispense. This prevents the drive sleeve 30 from rotating with respect to the main housing 4 though it is still free to move axially with respect thereto. This deformation is subsequently used to urge the clicker 50, and the clutch 60, back along the drive sleeve 30 to restore the connection between the clutch 60 and the dose dial sleeve 70 when pressure is removed from the button 82.

Figure 14:
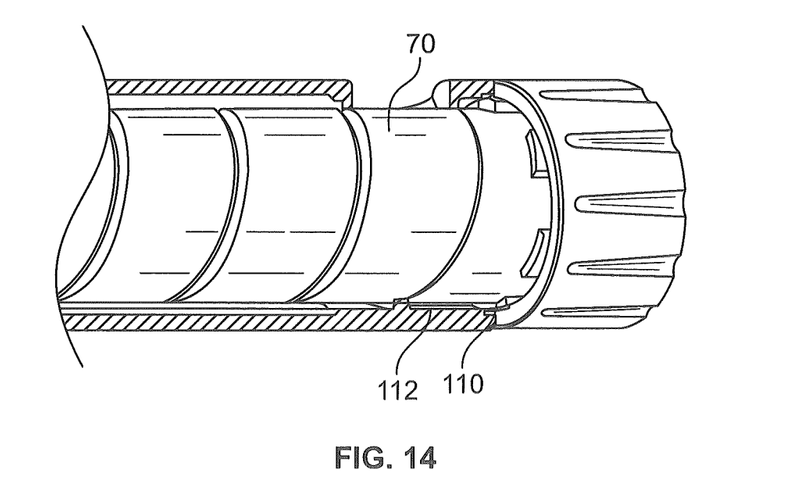
FIG. 14 shows a partially cut-away view of the pen-type injector of FIG. 1 in one of the first, third or fifth positions.

The longitudinal axial movement of the drive sleeve 30 causes the piston rod 20 to rotate though the opening 18 in the insert 16, thereby to advance the piston 10 in the cartridge 8. Once the dialed dose has been dispensed, the dose dial sleeve 70 is prevented from further rotation by contact of a plurality of members 110 (FIG. 14) extending from the dose dial grip 76 with a corresponding plurality of stops 112 formed in the main housing 4 (FIGS. 15 and 16). In the illustrated embodiment, the members 110 extend axially from the dose dial grip 76 and have an inclined end surface. The zero dose position is determined by the abutment of one of the axially extending edges of the members 110 with a corresponding stop 112.

The invention claimed is:

1. A drive mechanism for use in a drug delivery device comprising:
  a housing having a longitudinal axis and comprising an inner surface with an insert that is rotationally and axially fixed relative to the housing;
  a piston rod positioned and aligned with the longitudinal axis having a first thread on a first end that is engaged with the insert; and
  a drive sleeve that extends about the piston rod and has internal and outer surfaces, where the internal surface is engaged with the piston rod;

wherein longitudinal axial movement of the drive sleeve causes the piston rod to rotate through the insert relative to the housing.

2. The drive mechanism of claim 1 where the rotation of the piston rod advances a piston in a cartridge.

3. The drive mechanism of claim 1 where the piston rod has a second thread on a second end.

4. The drive mechanism of claim 3 where the drive sleeve has an internal surface comprising a helical groove that engages the second thread of the piston rod.

5. The drive mechanism of claim 4 further comprising a dose dial sleeve having an outer surface having a helical thread with a lead, where the helical groove of the drive sleeve has a lead that is equal to the lead of the helical thread of the helical thread on the dose dial sleeve.

6. The drive mechanism of claim 5 where the first thread and second thread have opposing directions to prevent the piston rod from rotating when the dose dial sleeve is extended axially from the housing.

7. The drive mechanism of claim 3 where the first thread has a different lead than the second thread.

8. The drive mechanism of claim 3 where the second thread comprises a series of part threads.

9. The drive mechanism of claim 3 where the first thread of the piston rod is oppositely disposed to the second thread of the piston rod.

10. The drive mechanism of claim 3 where the piston rod further comprises a receiving recess at the second end that accepts a stem of a button.

\* \* \* \* \*